Figure 1:
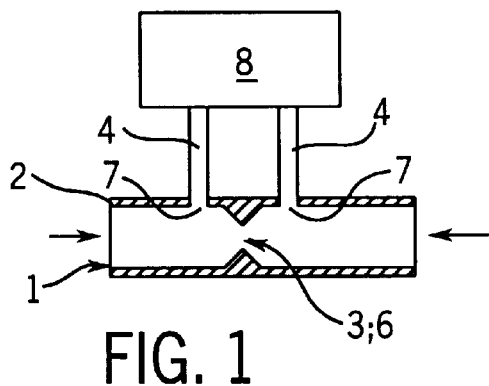

United States Patent
Weckström et al.

[11] Patent Number: 6,142,148
[45] Date of Patent: Nov. 7, 2000

[54] MEASURING DETECTOR AND SYSTEM FOR THE MEASUREMENT OF GAS FLOW

[75] Inventors: Kurt Weckström; Antti Kleemola, both of Espoo, Finland

[73] Assignee: Instrumentarium Corp., Helsinki, Finland

[21] Appl. No.: 09/180,834

[22] PCT Filed: Mar. 13, 1998

[86] PCT No.: PCT/FI98/00230
§ 371 Date: Nov. 16, 1998
§ 102(e) Date: Nov. 16, 1998

[87] PCT Pub. No.: WO98/41148
PCT Pub. Date: Sep. 24, 1998

[30] Foreign Application Priority Data

Mar. 17, 1997 [FI] Finland ................................. 971117

[51] Int. Cl.⁷ .................................................. A61M 16/00
[52] U.S. Cl. ................................ 128/204.22; 128/204.23
[58] Field of Search ........................ 128/204.22, 204.23; 73/861.52, 861.65; 600/531, 532, 543

[56] References Cited

U.S. PATENT DOCUMENTS

| | | | |
|---|---|---|---|
| 3,960,142 | 6/1976 | Elliot et al. | 128/2.08 |
| 4,197,857 | 4/1980 | Osborn | 128/718 |
| 4,403,514 | 9/1983 | Osborn | 73/861.52 |
| 4,932,269 | 6/1990 | Cammarata, III et al. | 73/861.61 |
| 5,088,332 | 2/1992 | Merilainen et al. | 73/861.65 |
| 5,111,827 | 5/1992 | Rantala . | |
| 5,134,890 | 8/1992 | Abrams | 73/861.52 |
| 5,676,132 | 10/1997 | Tillotson et al. | 128/204.23 |
| 5,789,660 | 8/1998 | Kofoed et al. | 73/23.2 |
| 5,858,514 | 1/1999 | Bowers | 428/195 |
| 5,913,249 | 6/1999 | Weckstrom | 73/861.52 |

FOREIGN PATENT DOCUMENTS

| | | |
|---|---|---|
| 257935 | 3/1988 | European Pat. Off. . |
| 549266 | 6/1993 | European Pat. Off. . |
| 96/02187 | 3/1996 | WIPO . |

OTHER PUBLICATIONS

Japan Patent Abstract No. JP62132117, dated Jun. 15, 1987 and English translation

*Primary Examiner*—Aaron J. Lewis
*Assistant Examiner*—Teena Mitchell
*Attorney, Agent, or Firm*—Andrus, Sceales, Starke & Sawall, LLP

[57] ABSTRACT

Measuring transducer and system for the measurement of gas flow, especially for the measurement of the pressure and/or flow of a patient's respiratory gas. The surface of the flow channel (1) wall (2) and/or a restricting element (3) in the flow channel which is directly exposed to the gas flow to be measured is provided with a material retaining water inside it.

39 Claims, 3 Drawing Sheets

MEASURING DETECTOR AND SYSTEM FOR THE MEASUREMENT OF GAS FLOW

The present invention relates to a measuring transducer for the measurement of gas flow, especially for the measurement of the pressure and/or flow of a patient's respiration, as defined in the preamble of claim 1. The invention further relates to a system for the measurement of the pressure and/or flow of a patient's respiration, as defined in the preamble of claim 20.

In hospitals, during intensive care and operations, respiration apparatus must be used to take care of the patients' respiration. Unhindered flow of gases into and out of the patient's lungs is naturally of vital importance. The condition of the gas channels can be monitored both by measuring the concentrations of the exhalation gases and by measuring the flow and pressure of the gases. Especially, monitoring of the carbon dioxide content of exhalation gas is widely used as a routine in operating theaters. However, flow and pressure measurements are essential additional functions both in respect of safety and because they make it possible to calculate quantities descriptive of the mechanical operation and respiratory metabolism of the lungs.

In principle, there are many applicable types of flow transducers. However, measurements in clinical conditions involve many problems. The flow is measured from the end of a so-called incubation tube inserted into the patient's windpipe. The transducer is therefore exposed to both humidity and mucous secretions coming from the windpipe. It is clear that such soiling is likely to affect the operation of especially the commonly used turbine and hot-wire transducers. Ultrasonic transducers are better able to tolerate soiling, but they are dependent on changes of the flow profile, temperature and gas composition, requiring sophisticated compensation. Differential pressure transducers are better suited for clinical use. The flow in the tube may be laminar or turbulent. In the case of laminar flow, the pressure difference across a flow restricting element placed in the tube is directly proportional to the flow. In the case of a turbulent flow, the pressure difference depends on the square of the flow. In addition, the pressure difference depends on the square of the cross-sectional area of the flow tube. The transducers currently used are generally made of plastic, and the concentration of water forms small drops on the interior walls of the flow transducer because water has a large contact angle to a plastic surface. The problem is that the condensed water together with possible secretions gathered in it reduce the cross-sectional area of the transducer, resulting in an increase in the measured pressure difference. If the measured pressure difference is too large, this also means that the calculated flow value is too high and therefore incorrect. A transducer with a small cross-sectional area is most sensitive in this respect. In short-time use of the measuring transducer, the resulting error is generally not too large, but if the transducer is used continuously e.g. for one or more hours in humid conditions, the error in the measurement results will be considerable. One way to eliminate this problem is to heat the transducer to a temperature sufficient to prevent condensation. However, this method requires a heating element and an electric connection, so it is difficult to use in practice and a transducer with a heating element is also expensive to fabricate. Moreover, a hot element may involve a danger to the patient.

The object of the present invention is to eliminate the problems described above.

A specific object of the invention is to present an improved transducer restricting the flow of respiratory gas which is not sensitive to condensed water and the patient's mucous secretions and which is capable of reliable operation even in dirty conditions. A further object of the invention is to present a system correspondingly improved for the measurement of the pressure and/or flow of a patient's respiration.

The measuring transducer of the invention is characterized by what is presented in claim 1. The system of the invention is characterized by what is presented in claim 20.

The measuring transducer of the invention comprises a tubular flow channel for conveying the gas flow to be measured, which flow channel is delimited by a wall; a restricting element disposed in the flow channel to restrict gas flow in the flow channel; and measuring channels opening into the flow channel for the measurement of the pressure difference caused by the restricting element.

According to the invention, a surface of the flow channel wall and/or of the restricting element that is in direct contact with the gas flow to be measured is provided with a material retaining water inside it for removing water drops or water containing drops from the surface of said material. The material may be either a capillary-porous material or a colloid. Moreover, it may also be hygroscopic, though not necessarily. In porous materials, the capillary force retains water and if the material is additionally hygroscopic, then water is largely physically bound to the surface of either the material or the pores in it (adsorption) or inside the material (absorption). This property is generally termed water sorption because it may be difficult to determine whether it is adsorption or absorption that is involved in a particular case. A colloid does not actually contain any pores but a sort of microscopic filaments that retain water between them. Typically the water is physically bound.

The system of the invention comprises an incubation tube designed to be inserted into a patient's windpipe; a measuring transducer connected to the incubation tube and comprising a tubular flow channel for conveying the gas flow to be measured, said flow channel being delimited by a wall; a restricting element disposed in the flow channel to restrict gas flow in the flow channel; a measuring device for measuring the pressure difference caused by the restricting element; and measuring channels opening into the flow channel for passing the pressure from the flow channel to the measuring device.

According to the invention, the surface of the flow channel wall and/or the restricting element, said surface being in direct contact with the gas flow to be measured, is provided with a material retaining water inside it for removing water drops or water containing drops from the surface of said material in service conditions. These service conditions are of a nature problematic to a flow meter, i.e. they include a high relative humidity and consequent condensation of water on the interior surface of the transducer. A patient's respiration air is a typical example of this type of environment.

The invention is based on the principle of influencing the behaviour of water on the surface of the transducer material by using a material retaining water inside it so as to cause condensed drops to be absorbed and to spread along the interior surface of the measuring transducer, thus preventing excessive reduction of the cross-sectional area of the transducer. Therefore, even small water drops quickly combine with each other, forming a continuous film which can flow out of the transducer. The flow reading will remain within the set tolerance limit for a long time, which is important especially in intensive care. The phenomenon is similar to the situation where the contact angle between water and the material is small. However, in the case of a material retaining water inside it the value of the contact angle is not of a decisive importance.

In an embodiment of the measuring transducer and system, the material retaining water inside it is a capillary-porous, non-hygroscopic material. In this case, the transducer must be moistened before use and care must be taken to keep it moist during use. Sand and similar materials are good examples of such materials.

In an embodiment of the measuring transducer and system, the material retaining water inside it is a capillary-porous, non-hygroscopic material with some hygroscopic material added to it to allow faster initial moistening.

In an embodiment of the measuring transducer and system, the material retaining water inside it is a capillary-porous and hygroscopic material. In this case the material will be readily saturated with water in a moist environment, and the capillary force promotes the saturation.

In an embodiment of the measuring transducer and system, the material retaining water inside it is a colloid. Typically, such colloids are hygroscopic and able to form a gel with water, e.g. gelatine and agar—agar.

In an embodiment of the measuring transducer and system, the material retaining water inside it, when under water saturation pressure, is able to absorb an amount of water exceeding 20% of its weight, advantageously over 50%, preferably over 100% of its weight.

In an embodiment of the measuring transducer and system, the material retaining water inside it forms a film-like coating on the surface in question.

In an embodiment of the measuring transducer and system, the coating formed from the material retaining water inside it is immobilized on the surface.

In an embodiment of the measuring transducer and system, substances promoting adhesion to the surface have been added to the coating formed from the material retaining water inside it.

In an embodiment of the measuring transducer and system, the material of the wall and/or restricting element is impregnated with active material.

In an embodiment of the measuring transducer and system, substances improving durability have been added to the coating formed from the material retaining water inside it.

In an embodiment of the measuring transducer and system, the surface has been treated so as to make it porous.

In an embodiment of the measuring transducer and system, the transducer has been formed from a material retaining water inside it, e.g. from a porous material.

In an embodiment of the measuring transducer and system, the measuring transducer is a spirometer transducer connected to an incubation tube inserted into the patient's windpipe. The transducer may also comprise a measuring channel incorporated in the same piece and functioning as a sampler for a gas analyzer. The measuring channel can be coated with a material retaining water inside it.

In an embodiment of the measuring transducer and system, a measuring channel functioning as a sampler for a gas analyzer is connected to the measuring transducer.

In an embodiment of the measuring transducer and system, the measuring transducer is a transducer working on the Pitot tube principle, based on the measurement of Pitot pressure, in which the flow restricting element consists of one or more vanes directed against the flow.

In an embodiment of the measuring transducer and system, the restricting element is provided with radial vanes arranged around the orifice of the measuring channel, and each vane is provided with a groove for directing the gas flow impinging on the vanes into the orifice.

In an embodiment of the system, the system comprises a gas analyzer for the determination of the composition of respiratory gas.

In an embodiment of the system, the measuring channel functioning as a sampler for a gas analyzer is disposed between the incubation tube and a respiration apparatus.

In an embodiment of the system, the measuring channel functioning as a sampler for a gas analyzer is disposed between a respiration apparatus and the patient.

Figure 2:
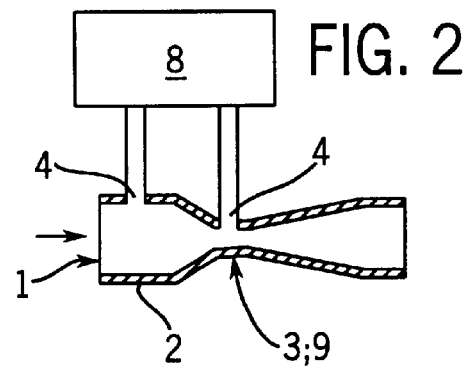
Figure 3:
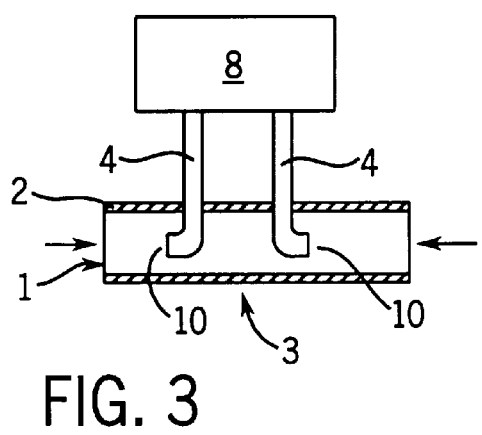
Figure 4:
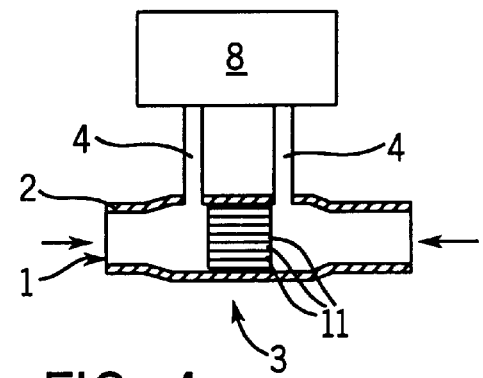
Figure 5:
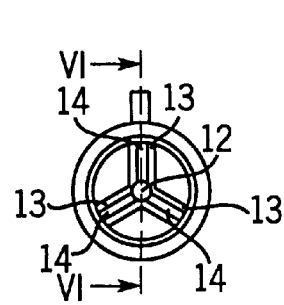
Figure 6:
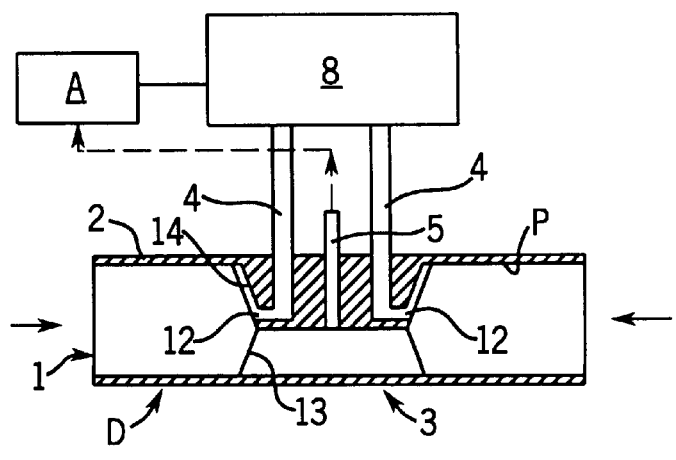
Figure 7:
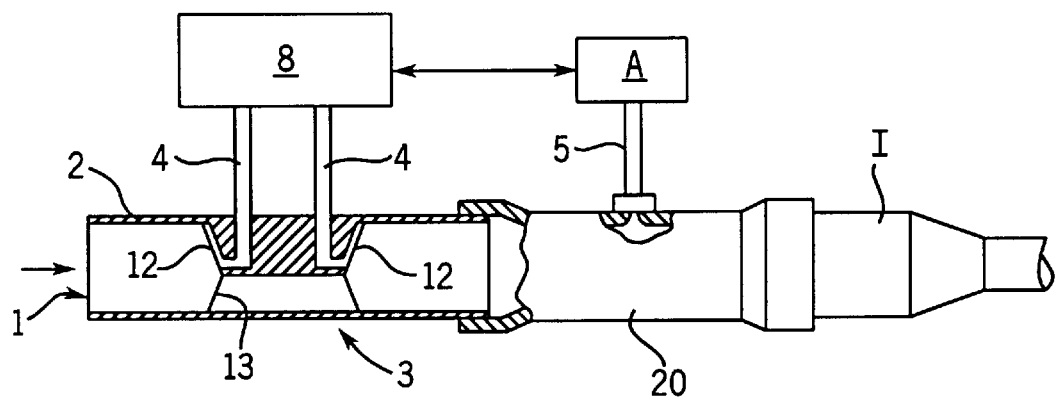
Figure 8:
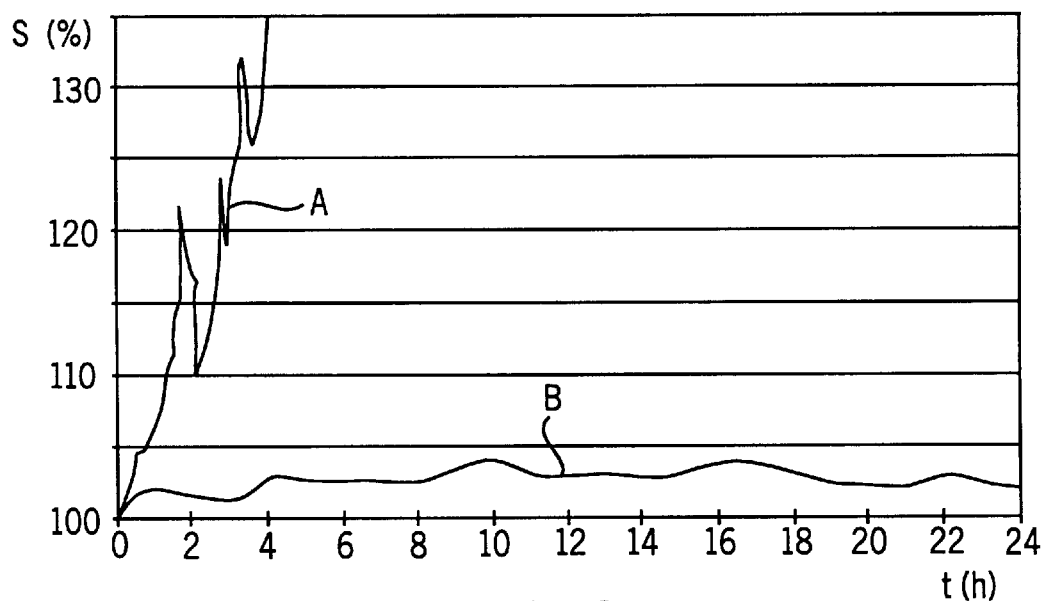
Figure 9:
Figure 10:
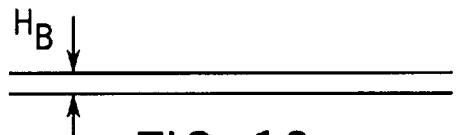
Figure 11:
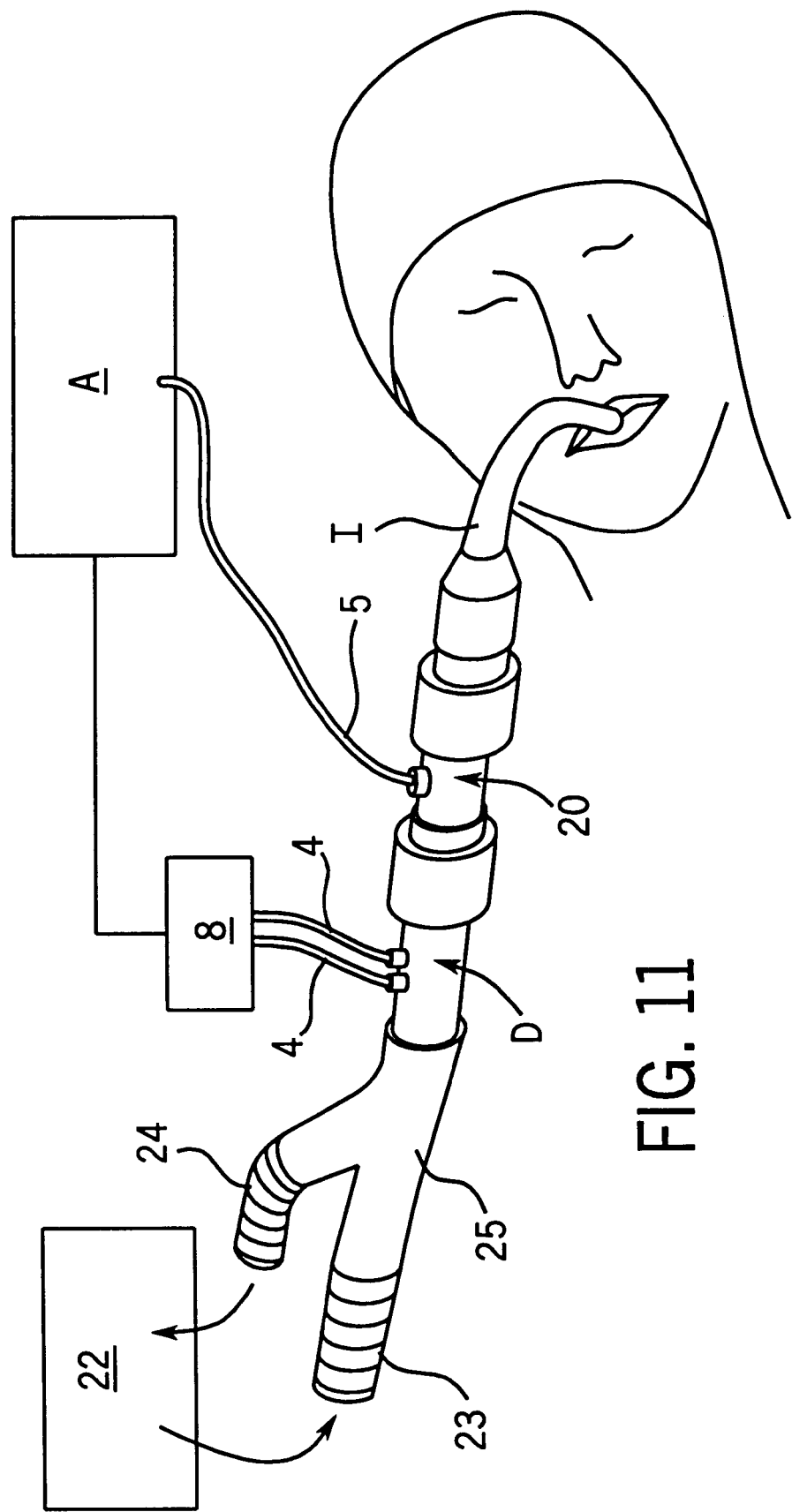

In the following, the invention is described in detail by the aid of a few examples of its embodiments by referring to the attached drawing, in which FIG. 1 is a diagram representing a first embodiment of the measuring transducer of the invention in longitudinal section, FIG. 2 is a diagram representing a second embodiment of the measuring transducer of the invention in longitudinal section, FIG. 3 is a diagram representing a third embodiment of the measuring transducer of the invention in longitudinal section, FIG. 4 is a diagram representing a fourth embodiment of the measuring transducer of the invention in longitudinal section, FIG. 5 is a diagram representing a fifth embodiment of the measuring transducer of the invention in longitudinal section, FIG. 6 presents section VI—VI of FIG. 5, FIG. 7 is a diagram representing a sixth embodiment of the measuring transducer of the invention in longitudinal section, FIG. 8 presents signals measured with an uncoated measuring transducer A and with a measuring transducer B coated with a material retaining water inside it as provided by the invention, as functions of time, FIG. 9 illustrates the shape of a couple of water drops on the surface a wall of a prior-art measuring transducer, FIG. 10 illustrates the shape of a water drop on the surface of a transducer wall treated with a material retaining water inside it according to the invention, and FIG. 11 is a diagram representing an embodiment of the system of the invention.

FIG. 1–7 present different types of measuring transducers with flow restriction, designed for the measurement of gas flow, which can be improved with a coating of active material according to the invention. The main types of flow transducer and their principles are presented e.g. in the publication Doebelin: Measurement Systems, McGraw-Hill Kogakusha, 1976, which is referenced here.

The measuring transducers presented in FIG. 1–7 comprise a tubular flow channel 1 for conveying a gas flow to be measured. The flow channel is delimited by a wall 2. The flow channel is provided with a restricting element 3 to restrict gas flow in the flow channel 1. Communicating with the flow channel 1 are measuring channels 4, which are connected to a measuring device for the measurement of the pressure difference created in the flow channel by the action of the flow restricting element 3. The surface of the flow channel 1 wall 2 and/or restricting element 3 which is directly exposed to the gas flow to be measured is provided with a material retaining water inside it in order to retain water in said surface so that no water drops can be formed and the flow channel diameter remains almost unchanged. The action is based on a high water retention capacity of the material, and the material or material mixture is generally and preferably hygroscopic.

In the embodiment illustrated by FIG. 1, the restricting element 3 restricting the flow in the flow channel 1 is an aperture 6, with the orifices 7 of the pressure measuring channels 4 on both sides of it. These orifices are connected via measuring channel tubes 4 to a measuring device 8, which is an element measuring pressure difference. As to its shape, the aperture 6 may have different appearances as stated in the above-mentioned publication, but its sensitivity to condensed water is the same in all embodiments, the restricting aperture being the most critical part because of the smallest diameter.

As shown in FIG. 2, the restricting element 3 may also consist of a narrowed part 9 in the flow channel 1. This is a so-called Venturi tube, in which the losses are somewhat smaller because of the streamlined design. Its sensitivity to moisture is, however, the same as in a transducer with a restricting aperture as shown in FIG. 1.

FIG. 3 presents a flow measuring transducer in which the restricting element 3 restricting flow in the flow channel consists of the measuring channel 4 orifices 10, which are placed in the flow. The orifices 10 are symmetrically arranged to permit flow measurement in both directions of the tube with the same sensitivity. The orifices 10, typically located in the centre of the flow channel tube 1, are connected to a measuring device 8 via measuring channel tubes 4. The orifices 10 are a variation of the Pitot tube. A transducer like this has a relatively low flow resistance, but in the case of an uneven flow profile, a measurement error will be produced. This is what occurs for instance in respiratory tract measurement, as is stated in U.S. Pat. No. 5,088,332. This solution is somewhat less sensitive to condensed water, but in principle its behaviour is similar to that of the transducers mentioned above.

The flow transducer presented in FIG. 4 is based on laminar flow resistance. The restricting element 3 restricting flow has been constructed by dividing the interior space of the tube into a large number of small tubes 11, in each of which the flow remains laminar in the relevant measurement range. However, as a consequence, the transducer is liable to be blocked. It is clearly more sensitive to water drops than the other transducer types described.

Based on the principle illustrated by FIG. 3, FIG. 5 and 6 present an improved flow measuring transducer D with a construction known from U.S. Pat. No. 5,088,332, which measures the mean value of the flow profile. FIG. 5 shows the transducer in end view and FIG. 6 presents a longitudinal section of it, taken along line VI—VI. Placed near and around the orifices 12 acting as a restricting element 3 in the flow channel tube 1 are vanes 13 provided with a groove, this embodiment having three such vanes. This arrangement gathers the Pitot pressure evenly from all directions, and shifts in the flow profile have no effect on the result. It is also possible to connect to the transducer a sampling tube 5 for the measurement of gas concentrations, and the transducer is therefore a combination of a spirometer and a sampling adapter for a gas analyzer A.

FIG. 7 shows yet another embodiment of the measuring transducer, which corresponds to the transducer in FIG. 5 and 6 except that the measuring channel constituting a sampler connected to a gas analyzer A, is disposed on a separate connection piece 20 connected between the incubation tube I and the measuring transducer, corresponding to the system illustrated by FIG. 11, which will be described in more detail later on.

The transducer in FIG. 6 is sensitive to condensed moisture especially in measurements taking a long time. The transducer material is preferably plastic, e.g. polysulfone. Water gathers on the surface of this material, like most other plastic materials, in the form of drops. The situation is illustrated by FIG. 9. The drop height H directly reduces the diameter of the flow transducer by the amount of about 2.H. It will therefore be readily understood that the height $H_B$ of the water absorbed in the material retaining water inside it as presented in FIG. 10 has a much smaller effect because no actual water drops can be formed as the water is spread all over the surface of the material. How small a height $H_B$ will be reached depends on the thickness of the material used and on how much it swells when wet and on the thickness of the film of water or the water-containing film on the material. Thus, water will still be condensed on the transducer surface, but no drops can be formed and the extra water will readily flow away from the transducer area. The properties of the material to be used are also to be considered with reference to the measurement tolerance aimed at. Of course, it will be preferable to use a film as thin as possible, but on the other hand the film must be durable and it must not wear off or dissolve too fast in storage or service conditions. An ideal material for flow measurement of respiration air is a material that remains dry during storage and is quickly activated in service conditions when the temperature is close to the body temperature and relative humidity is close to 100%. The material is especially suitable for throwaway use because it can be cheap and harmless to the organism. Suitable colloids are e.g. gelatine and agar—agar, treated with a hygroscopic substance such as calcium chloride to ensure faster initial moistening. The use of a special moistening operation to activate the surface material could also be considered.

FIG. 8 presents a couple of measuring periods as a function of time, measured with a transducer as shown in FIG. 6. The vertical axis in FIG. 8 represents the flow signal S as a percentage of an initial value, while the horizontal axis represents time in hours. The gas used has been fully moistened at patient temperature, so condensation has occurred, even in a very large measure. Curve A has been measured using a measuring transducer without a coating of water-absorbing material. A more detailed description of the transducer and the associated measuring arrangement is to be found in specification U.S. Pat. No. 5,088,332. FIG. 8 shows that the flow signal S has increased by about 5% in the course of an hour. At 2 h, 2.6 h and 3.2 h, some small drops have combined into a large one and flown out of the transducer. The largest error measured during two hours from the beginning of the test is 20% and the signal varies all the time due to the periodic water outflow. In bad conditions, it may take as long as six hours for the signal to stabilize while the error is over 50%. Curve B has been measured using a transducer whose interior surface has been treated with a material retaining water inside it. In other words, the situation has been as in FIG. 10 instead stead of FIG. 9. The signal represented by curve B at first rises rapidly to about 2% due to the material swelling as it is saturated with water. After that, the signal error does not rise above the value of 5% during a complete diurnal cycle, which can be considered an accuracy requirement. The small variations in the curve are due to the periodic outflow from the transducer. The transducer used in this test had a coating of a material combination containing gelatine, agar—agar and calcium chloride. The substances are first dissolved in hot water in the ratio 0.5/2/2%, whereupon the interior parts of the transducer are coated with a thin film and the transducer is dried. If desirable, a solution with additional materials such as preservatives and components improving adhesion can be used. At the beginning of the test, the calcium chloride rapidly absorbs moisture from the respiration air and promotes the formation of gel from the gelatine. As gelatine as such is slow to dissolve in water at body temperature, agar—agar has been added to bind the gelatine. In this way, a coating is obtained that is soon ready for use and durable in continuous use. The test shows clearly that a coating retaining water inside it is of decisive importance in long-time use of the transducer.

A coating retaining water inside it should preferably be provided on the interior surfaces of the entire transducer, but the most critical surfaces are those where the flow restricting element 3 is located and where the cross-sectional area is smallest. A coating or impregnation of the transducer material with a material retaining water inside it can be applied to all the transducers presented in FIG. 1–7.

The retention capacity of the material retaining water inside it depends on the structure of the material used. If it is a capillary-porous and non-hygroscopic material, then as much water can be absorbed as the pores can hold, because the material itself does not absorb water. The upper limit for this amount of water is obviously the volume of the material. No swelling occurs, so the signal error should remain small throughout the measurement. However, the material will not work unless the capillaries are filled with water. This can be achieved either via preliminary moistening or by using a hygroscopic material such as calcium chloride to accelerate initial moistening in a humid environment. A transducer with a coating of this type of material could easily be sterilizable because it can be so implemented that it will tolerate a high temperature.

Water sorption in a non-hygroscopic coating material is generally very low because water is not bound with the material, whereas for a hygroscopic material water sorption is an essential property. As stated before, water can be absorbed into a material or it can be adsorbed to the surface or surface structure of the material. Moreover, the porosity of the material influences its water retention through the capillary effect, and its hygroscopicity determines the ability of the material to absorb moisture from ambient air. Water sorption in a material is generally measured in different humidity conditions as the proportion of the amount of water to the amount of material. Because the component water pressure in service conditions is very close to the saturation pressure, readily permitting condensation, water sorption in the material at water saturation pressure is an important property. When the amount of water a material can absorb is 20% of its own weight, it can be considered that the growth of water drops on the surface of the material is substantially prevented, especially if a hygroscopic material is used at the same time to accelerate water saturation. A more advantageous situation is obtained if water sorption in the material is over 50%, and the most advantageous alternative is the case where water sorption is over 100% water of the weight of the material, measured at saturation pressure. This applies e.g. for gelatine, but the consequent swelling of the material will not significantly impair the measuring accuracy if the coating is sufficiently thin, as is indicated by FIG. 8. Even though the hygroscopic material, i.e. calcium chloride in the material mixture is likely to dissolve at least partially during use, the transducer will still work well after the gelatine and agar—agar have turned into gel. Such a transducer could work e.g. for a few days, which in most cases is fully sufficient for a disposable transducer.

Besides allowing water to flow out more readily from the coated transducer, the more lubricious surface also allows easier removal of possible secretions. In the above description, only a few typical examples of measuring transducers using a flow restricting element are mentioned. It is obvious that even other types of transducers working on a corresponding principle will benefit from the use of a water retaining material improving measurement accuracy according to the present invention.

FIG. 11 presents a system according to the invention in practical use, with an incubation tube I inserted into a patient's windpipe. Connected to the respiratory circuit is a measuring transducer D corresponding to a spirometer transducer treated on the inside with an active material, as shown e.g. in FIG. 7. A connecting piece 20, provided with a measuring channel for the measurement of gas concentration, is connected between the incubation tube I and a Y-shaped piece 25 connecting the inlet and outlet hoses 23, 24 of an apparatus 22 maintaining respiration. The connecting piece 20 is normally so connected that it lies closest to the patient, but it could also be integrated with the flow transducer D as in FIG. 6 or it could be placed between the flow transducer and the Y-shaped piece 24. The gas sampler tube 5 is connected via a hose to a patient monitor or analyzer A, in which the gas is measured and the signal is processed so as to produce a display showing the variations in the gas concentration under measurement as a function of time, i.e. the respiration curve or concentrate on readings during inhalation and exhalation. The flow transducer is also connected via the measuring apparatus 8 to the analyzer A, in which the signal is processed so as to produce a display of the flow and pressure readings for inhalation and exhalation and possible other quantities derived therefrom. The measuring device 8 may also be placed in the analyzer A and the gas concentration measurement can be performed in the connecting piece 20.

The invention is not restricted to the examples of its embodiments described above, but many variations are possible within the framework of the inventive idea defined by the claims.

What is claimed is:

1. A measuring transducer for the measurement of gas flow, including the measurement of the pressure and/or flow of a patient's respiratory gas, which measuring transducer comprises:

a tubular flow channel (1) for conveying the gas flow to be measured, said flow channel being delimited by a wall (2) having an interior surface exposed to the gas flow to be measured;

a restricting element (3) disposed in the flow channel to restrict gas flow in the flow channel and presenting a surface exposed to the gas flow to be measured; and measuring channels (4) opening into the flow channel for the measurement of the pressure difference caused by the restricting element, at least one of said surface of the flow channel wall (2) and surface of the restricting element (3) being capable of retaining water inside it to remove water drops or drops containing water from said surface.

2. A measuring transducer as defined in claim 1, characterized in that said surface retaining water inside it is formed by a capillary-porous material.

3. A measuring transducer as defined in claim 1, characterized in that the surface retaining water inside it is formed by a colloid.

4. A measuring transducer as defined in claim 1, characterized in that the surface retaining water inside it is hygroscopic.

5. A measuring transducer as defined in claim 1, characterized in that the surface retaining water inside it is formed by a capillary-porous and non-hygroscopic material.

6. A measuring transducer as defined in claim 5, characterized in that a hygroscopic material has been added to the capillary-porous and non-hygroscopic material for faster initial moistening.

7. A measuring transducer as defined in claim 1, characterized in that the surface retaining water inside it is formed by a mixture of materials having hygroscopic and water retaining properties.

8. A measuring transducer as defined in claim 1, characterized in that the surface is formed by a water retaining material that, at water saturation pressure, is able to absorb an amount of water exceeding 20% of its weight, advantageously exceeding 50% of its weight, preferably exceeding 100% of its weight.

9. A measuring transducer as defined in claim 1, characterized in that the surface is formed by a material retaining water inside it comprising agar—agar, gelatine and/or calcium chloride.

10. A measuring transducer as defined in claim 1, characterized in that the surface is formed by a material to which has been added a substance improving its durability.

11. A measuring transducer as defined in claim 1, characterized in that a material retaining water inside it forms a film-like coating (P) on said at least one of said surfaces.

12. A measuring transducer as defined in claim 11, characterized in that the coating (P) formed from the material retaining water inside it is immobilized on said at least one of said surfaces.

13. A measuring transducer as defined in claim 1, characterized in that at least one of said wall (2) and restricting element (3) is impregnated with a material retaining water inside it.

14. A measuring transducer as defined in claim 1, characterized in that the said at least one of said surfaces is treated so as to make it porous.

15. A measuring transducer as defined in claim 1, characterized in that the transducer is formed from a material retaining water inside it.

16. A measuring transducer as defined in claim 1, characterized in that the measuring transducer (D) is a spirometer transducer suitable for connection to an incubation tube (I) that can be inserted into a patient's windpipe.

17. A measuring transducer as defined in claim 16, characterized in that a measuring channel (5) functioning as a sampler for a gas analyzer (A) is formed in the measuring transducer (D).

18. A measuring transducer as defined in claim 1, characterized in that the measuring transducer (D) is a transducer working on the Pitot tube principle, based on the measurement of Pitot pressure, and in that the flow restricting element (3) comprises one or more vanes extending into said flow channel from said wall.

19. A measuring transducer as defined in claim 18, characterized in that the restricting element (3) is provided with radially extending vanes (13) arranged circumferentially around an orifice (12) of a measuring channel (4), and that each vane (12) has a groove (14) for directing the gas flow impinging on the vane into the orifice.

20. A system for the measurement of the pressure and/or flow of a respiratory gas of a patient, comprising;
an incubation tube (I) to be inserted into a patient's windpipe;
a measuring transducer (D) connected to the incubation tube and comprising a tubular flow channel (1) for conveying the gas flow to be measured, said flow channel being delimited by a wall (2) having an interior surface exposed to the gas flow to be measured;
a restricting element (3) disposed in the flow channel to restrict gas flow in the flow channel and presenting a surface exposed to the gas flow to be measured;
a measuring device (8) for measuring the pressure difference caused by the restricting element; and
measuring channels (4) opening into the flow channel for passing the pressure from the flow channel to the measuring device, at least one of said surface of the flow channel wall (2) and surface of the restricting element (3) being capable of retaining water inside it to remove water drops or drops containing water from said surface.

21. A system as defined in claim 20, characterized in that said surface retaining water inside it is formed by a capillary-porous material.

22. A system as defined in claim 20, characterized in that said surface retaining water inside it is formed by a colloid, such as gelatine or agar—agar.

23. A system as defined in claim 20, characterized in that the surface retaining water inside it is hygroscopic.

24. A system as defined in claim 20, characterized in that the surface retaining water inside it is formed by a capillary-porous and non-hygroscopic material.

25. A system as defined in claim 24, characterized in that a hygroscopic material has been added to the capillary-porous and non-hygroscopic material to achieve faster initial moistening.

26. A system as defined in claim 20, characterized in that the surface retaining water inside it is formed by a mixture of materials having hygroscopic and water retaining properties.

27. A system as defined in claim 20, characterized in that the surface is formed by a water retaining material that, at water saturation pressure, is able to absorb an amount of water exceeding 20% of its weight, advantageously exceeding 50% of its weight, and preferably exceeding 100% of its weight.

28. A system as defined in claim 20, characterized in that the surface is formed by a material retairing water inside it comprising agar—agar, gelatine and/or calcium chloride.

29. A system as defined in claim 20, characterized in that the surface is formed by a material retaining water inside it to which has been added a substance improving its durability.

30. A system as defined in claim 20, characterized in that a material retaining water inside it forms a film-like coating (P) on said at least one of said surfaces.

31. A system as defined in claim 30, characterized in that the coating (P) formed from the material retaining water inside it is immobilized on said at least one of said surfaces.

32. A system as defined in claim 20, characterized in that at least one of said wall (2) and restricting element (3) is impregnated with a material retaining water inside it.

33. A system as defined in claim 20, characterized in that the surface of said at least one of said flow channel or restricting element is treated so as to make it porous.

34. A system as defined in claim 20, characterized in that the measuring transducer (D) is formed from a material retaining water inside it.

35. A system as defined in claim 20, characterized in that the measuring transducer (D) is a spirometer transducer.

36. A system as defined in claim 35, characterized in that it includes a gas analyzer (A) for the determination of the composition of the respiratory gas and that a measuring channel (5), arranged to function as a sampler for said gas analyzer (A), is connected to the measuring transducer (D).

37. A system as defined in claim 20, characterized in that the measuring transducer (D) is a transducer working on the Pitot tube principle, based on the measurement of Pitot pressure, and in that the flow restricting element has one or more vanes (13) acting as flow restricting elements (3), said vane or vanes extending into the flow channel from said wall.

38. A system as defined in claim 20 wherein respiratory gas for the patient is supplied by respiration apparatus, said system being characterized in that the system further comprises a gas analyzer (A) for the determination of the composition of respiratory gas and in that a measuring channel functioning as a sampler for the gas analyzer is disposed between the respiration apparatus and the patient.

39. A system as defined in claim 38, characterized in that the measuring channel (5) functioning as a sampler for the gas analyzer (A) is disposed between the incubation tube (I) and the respiration apparatus (22).

* * * * *

UNITED STATES PATENT AND TRADEMARK OFFICE
CERTIFICATE OF CORRECTION

PATENT NO. : 6,142,148
DATED : November 7, 2000
INVENTOR(S) : Kurt Weckström et al.

It is certified that error appears in the above-identified patent and that said Letters Patent is hereby corrected as shown below:

Column 2,
Lines 34 and 36, delete "incubation" and substitute therefor -- intubation --;

Column 3,
Line 52, delete "incubation" and substitute therefor -- intubation --;

Column 4,
Line 8, delete "incubation" and substitute therefor -- intubation --;

Column 5,
Lines 61 and 62, delete "incubation" and substitute therefor -- intubation --;

Column 8,
Lines 7 and 13, delete "incubation" and substitute therefor -- intubation --;

Column 9,
Lines 41, 61 and 63, delete "incubation" and substitute therefor -- intubation --;

Column 10,
Line 38, delete "retairing" and substitute therefor -- retaining --;

Column 12,
Line 6, delete "incubation" and substitute therefor -- intubation --.

Signed and Sealed this

Twenty-eighth Day of January, 2003

JAMES E. ROGAN
*Director of the United States Patent and Trademark Office*